United States Patent [19]

Munakata et al.

[11] Patent Number: 4,720,506
[45] Date of Patent: Jan. 19, 1988

[54] IMMUNOMODULATING AGENT

[75] Inventors: Hiroaki Munakata, Sagamihara; Makio Kobayashi, Machida; Kazuo Wagatsuma, Machida; Shigeru Sato, Machida; Makoto Tsurufuji, Tokyo; Hiroshi Enomoto, Kyoto; Makoto Sugiyama, Kyoto; Yoshihisa Shibata, Kyoto; Iwao Morita, Kyoto, all of Japan

[73] Assignees: Nippon Shinyaku Company, Limited, Kyoto; Mitsubishi Chemical Industries Limited, Tokyo, both of Japan

[21] Appl. No.: 45,161

[22] Filed: May 4, 1987

Related U.S. Application Data

[63] Continuation of Ser. No. 487,012, Apr. 21, 1983, abandoned.

[30] Foreign Application Priority Data

May 11, 1982 [JP] Japan .................................. 61-78893

[51] Int. Cl.$^4$ ........................................... A61K 31/24
[52] U.S. Cl. .................... 514/538; 514/563; 514/567
[58] Field of Search ...................... 514/538, 563, 507; 560/19; 502/433

[56] References Cited

U.S. PATENT DOCUMENTS 3,641,040 2/1972 Carney et al. .................. 544/78

Primary Examiner—James H. Reamer
Attorney, Agent, or Firm—Oblon, Fisher, Spivak, McClelland & Maier

[57] ABSTRACT

Phenylacetic acid derivatives of the formula:

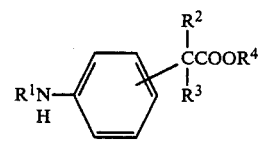

wherein $R^1$ is hydrogen or

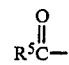

wherein $R^5$ is an alkyl group of 1–6 carbon atoms or an aryl group; $R^2$ and $R^3$ are independently hydrogen or an alkyl group of 1–4 carbon atoms; $R^4$ is hydrogen or an alkyl group of 1–4 carbon atoms, have been found to possess immunomodulating activity.

13 Claims, 1 Drawing Figure

IMMUNOMODULATING AGENT

This application is a continuation of Ser. No. 06/487,012, filed on Apr. 21, 1983, now abandoned.

BACKGROUND OF THE INVENTION

Field of the Invention

This invention relates to an immunomodulating agent.

SUMMARY OF THE INVENTION

This invention resides in the immunomodulating agent which contains a phenylacetic acid derivative of the formula (I):

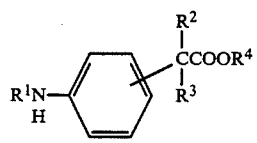

wherein $R^1$ is hydrogen or

wherein $R^5$ is an alkyl group of 1–6 carbon atoms or aryl group; $R^2$ and $R^3$ are independently hydrogen or an alkyl group of 1–4 carbon atoms; and $R^4$ is hydrogen or an alkyl group of 1–6 carbon atoms, and its pharmaceutically acceptable salts as effective ingredient.

The term "immunomodulating activity" used herein is intended to encompass both of immunosuppressive activity and immunostimulating activity.

DETAILED DESCRIPTION OF PREFERRED EMBODIMENTS

Figure 1:
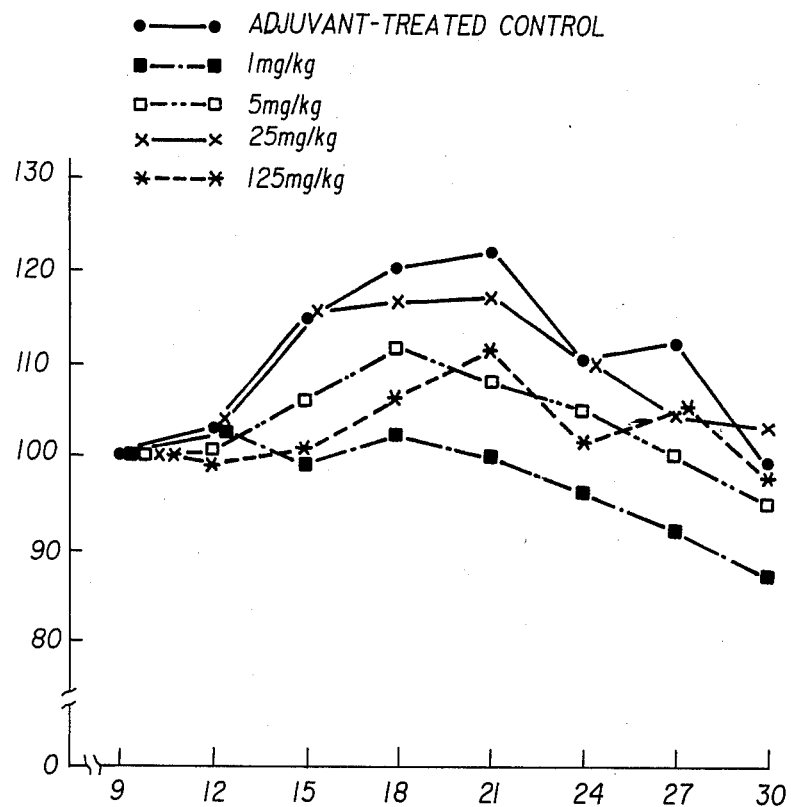
FIG. 1 is a graph to show the test results on rats adjuvant arthritis, and the horizontal axis represents the numbers of days after the adjuvant was injected and the perpendicular axis represents the relative swelling volume (%) to that on 9th day.

The compounds according to this invention are represented by the formula (I):

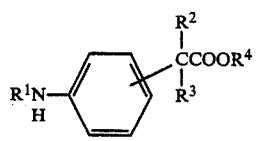

In Formula (I), the alkyl group of $R^1$ to $R^5$ may be any of a straight or branched alkyl group; they include methyl, ethyl, n-propyl, isopropyl, n-butyl, isobutyl, tert-butyl, n-pentyl group etc. The aryl group of $R^5$, include phenyl, tolyl, xylyl, naphthyl group etc.

The examples of the phenylacetic acid derivatives of Formula (I) are:

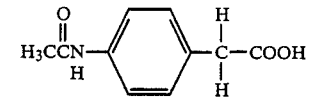

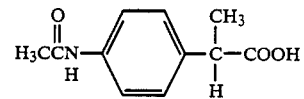

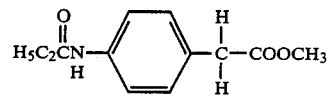

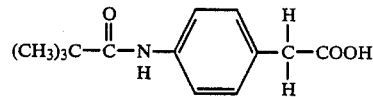

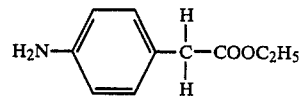

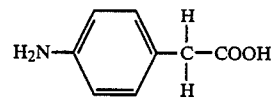

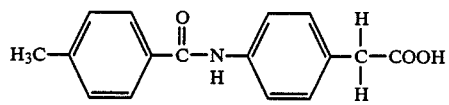

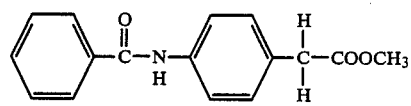

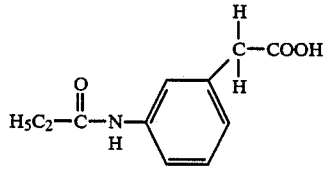

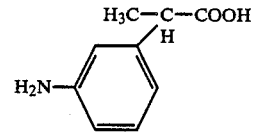

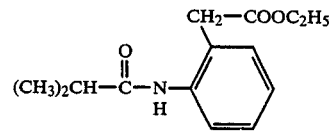

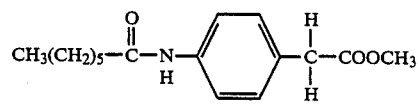

The salts of these phenylacetic acid derivatives of the formula (I) are pharmaceutically acceptable salts which include, for example, in the case where $R^1$ is

and R⁴ is hydrogen, salts with an inorganic base such as an alkali or alkaline earth metal, e.g., sodium, potassium, calcium, etc. and salts with an organic base such as procaine, N,N'-dibenzylethylenediamine, etc.; and in the case where R¹ is hydrogen and R⁴ is an alkyl group of 1–4 carbon atoms, acid addition salts such as hydrochloride, sulfate, fumarate, maleate, formate, etc.

The preparation methods of the compounds of the formula (I) of the present invention are described as follows: The preparation methods are explained by dividing into the compound of the formula (II) and the compound of the formula (III):

$$H_2N-\underset{}{\bigcirc}-\underset{R^3}{\overset{R^2}{\underset{|}{C}}}-COOR^4 \quad (II)$$

$$R^5-\overset{O}{\underset{\|}{C}}-NH-\underset{}{\bigcirc}-\underset{R^3}{\overset{R^2}{\underset{|}{C}}}-COOR^4 \quad (III)$$

wherein R² to R⁵ of Formulas (II) and (III) are as defined in Formula (I).

The aniline derivatives of the foregoing formula (II) can be prepared by various synthetic routes. For reference, examples of such synthetic routes are shown below.

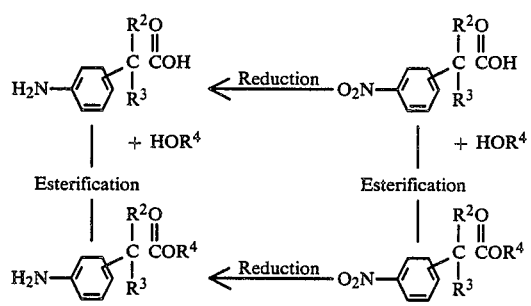

The reduction may be performed by catalytic hydrogenation using palladium, palladium black or palladium on charcoal. Alternatively, reduction with iron powder/NH₄Cl or the like may be applied.

The esterification may be conducted by heating along with the starting alcohol in the presence of hydrochloric, sulfuric or p-toluenesulfonic acid, if necessary, followed by azeotropic dehydration in the co-existence of an azeotropic dehydrating agent such as benzene, thereby readily providing the desired ester.

Nitrobenzene derivatives used as starting material can be synthesized by various synthetic routes. For reference, examples of such synthetic routes are shown below.

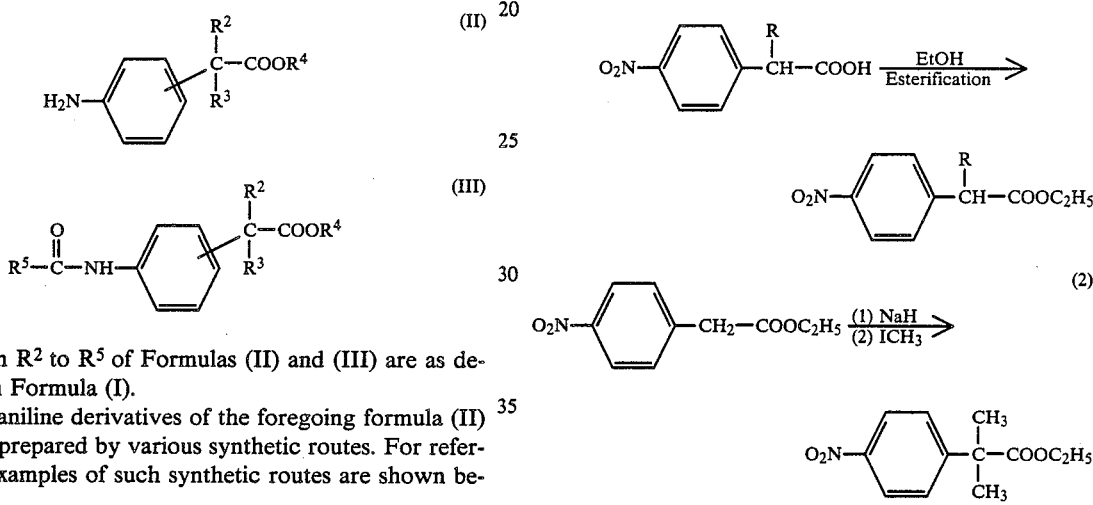

A diethyl 2-alkyl-2-(4-nitrophenyl)malonate in the above Process (1) can be obtained by reacting a 2-alkyl malonate with a strong base such as sodium hydride in N,N-dimethylformamide and then with p-halonitrobenzene.

Hydrolysis of the resulting ester may be effected by reaction with sodium hydroxide, potassium hydroxide or the like in water or an alcohol (methanol, ethanol, etc.) or a mixture thereof.

An α-alkyl-nitrophenylacetic acid can be obtained by heating a diethyl 2-alkyl-2-(4-nitrophenyl)malonate along with excess sodium hydroxide or potassium hydroxide in water or an alcohol (methanol, ethanol, etc.) or a mixture thereof, or by heating a 2-alkyl-2-(4-nitrophenyl)malonic acid along with a suitable acid such as hydrochloric, sulfuric or p-toluenesulfonic acid in a suitable solvent such as an alcohol (methanol, ethanol, etc.), benzene, or toluene.

The subsequent esterification may be performed by heating with ethanol in the presence of hydrochloric, sulfuric or p-toluenesulfonic acid.

Ethyl 2-methyl-2-nitrophenylpropionate in the above Process (2) can be obtained by reacting ethyl nitrophenylacetate with a strong base such as sodium hydride in N,N-dimethylformamide and then with excess methyl iodide.

The carboxylic acid of the formula (III), wherein R⁴ is a hydrogen atom, can be easily obtained from the corresponding ester such as methyl and ethyl ester by a conventional hydrolysis method.

The compound of the formula (III), wherein $R^4$ is an alkyl group can be prepared in any conventional manner. For instance, the compound of the foregoing formula (III) can be obtained by reacting an acid anhydride such as acetic anhydride and propionic anhydride with an aniline derivative of the formula (II):

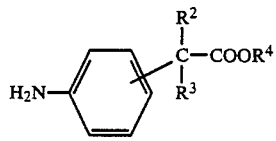
(II)

And the compound of the above formula (III) can be obtained by reacting a carboxylic chloride with an aniline derivative of the formula (II).

As the methods for preparing ethyl 4-acetylaminophenylacetate, the following two synthetic methods are shown by the reaction scheme:

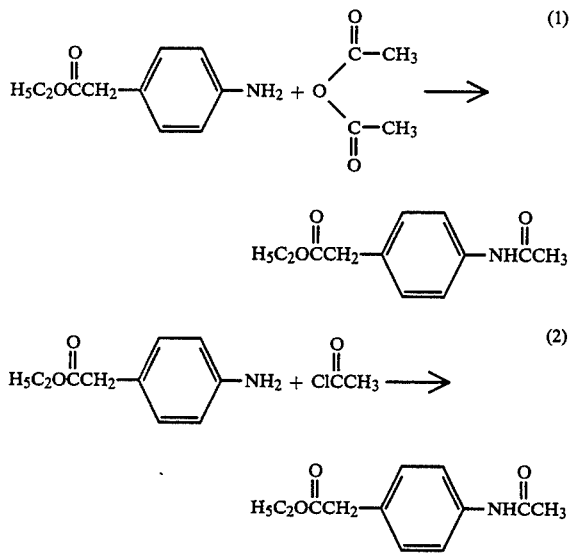

The desired compounds obtained by these processes may be purified by means of recrystallization, ion-exchange treatment, chromatography, activated charcoal treatment or the like, according to the conventional practice in organic chemistry.

Thus obtained compounds are used as the effective ingredients of immunomodulating agents of the present invention for the therapy and prevention of various diseases caused from immune reaction.

The immunomodulating agents of the present invention can be administered orally or parenterally (for instance, intramuscularly, subcutaneously, intravenously, rectally) in the form per se or various administration unit form.

As the solid preparations, tablets, sugar coated tablets, film coated tablets, enteric coated tablets, hard or soft gelatin capsules, troches, pills, granules, fine granules, powder may be prepared. As the semi-solid preparations, suppositories, endermics (transdermal system), ointments may be prepared.

As the liquid preparations, injections, syrups, solutions, inhalants, emulsions, suspensions etc. may be prepared.

As the additives of the solid preparations, diluents (for instance, lactose, starches, mannitol, calcium hydrogen phosphate, etc.), binder (for instance, cellulose derivatives, polyvinyl alcohol, polyethylene glycol, gelatin, arbaic gum, crystal cellulose, etc.), disintegrators (for instance, carboxymethylcellulose, crystal cellulose, hydroxypropylcellulose with low substitution degree, etc.), lubricant (for instance, magnesium stearate, talc, light silic anhydride, synthetic aluminium silicate, etc.), retard-solubilizing agent (for instance, paraffin, etc.), coating materials (for instance, polyvinylacetaldiethylaminoacetate, HA (Registered Trade Name), hydroxypropylmethylcellulose and its phthalate, Eudragit (Rohm & Haas), shellac, sucrose, precipitated calcium carbonate, talc, calcium hydrogen phosphate, etc.), plasticizer (for instance, castor oil, polyethylene glycol), lusting agent (for instance, carnauba wax) etc., are used.

As the base of the suppositories, polyethylene glycol, various kinds of vegetable fats and hardened vegetable oils, Witepsol (glycerol fatty acid ester, Dynamite, Nobel AG) etc., are used, and surface active agent may be mixed in these bases.

As the base of ointment, fats and oils base (for instance, fats and oils from animals and plants, waxes, vaseline, etc.), water-soluble base (for instance, polyethylene glycol, cetyl alcohol etc.) or emulsion base (for instance, o/w or w/o emulsion base consisting of fats and oils from animals and plants, or mineral oils or synthetic fats and oils and aqueous layer and surface active agents) etc. are used.

The liquid preparation can be prepared by dissolving, emulsifying or suspending in distilled water, a lower aliphatic alcohols such as ethyl alcohol, polyalcohols such as polyethylene glycol and polypropylene glycol, etc., dimethylacetamide or fats and oils, or in these mixture. In this case, as solubilizing, emulsifying or suspension agents, various kinds of surface active agents, arabic gum, gelatin, cellulose derivative may be used depend upon the purpose, and in addition to this, isotonicity such as sodium chloride, preservative such as p-hydroxybenzoic acid derivative, reversed soap etc., and furthermore, buffer, local anesthetics may be used.

In order to increase the stability, for instance, it may be good to preserve as frozen-dried powder and to dissolve it when using.

Any of the solid, semi-solid, liquid preparations as mentioned above may contain colors, perfumes, flavors, sweetnings and stabilizer.

These preparations can be modified to long-acting preparations or micro-capsules in any conventional manner. One or more kinds of the effective ingredients of the present invention may be generally contained at a ratio of 0.1–99%, usually 0.5–90% of the whole composition in the preparation.

In the preparations of the present invention, one or more other medicaments, for instance, non-steroidal analgesic, anti-inflammatory agents such as acetylsalicylic acid, indomethacine or phenylbutazone etc. may be used as combination therapy along with the effective ingredients of the present invention.

The oral administration is most common for the administration method, but rectal administration or transdermal administration may be applied, too.

The dose of the effective ingredient is commonly 1–3,000 mg per day for parenteral administration, and 1–3,000 mg per day for oral administration, but the dose may be lower or higher than said dose depend upon the ages, body weight, kinds of diseases or degree of symptoms. In the case of administering much more dose, it can be recommended to administer by dividing the dose into several times.

The immunomodulating agent of the present invention has low toxicity and may be used in therapy, for example, of the following diseases: autoimmune diseases such as chronic rheumatoid arthritis, systemic lupus erythematodes (SLE), collagen disease, etc.; allergic diseases such as asthma, etc.; cancer; bacterial infectious diseases and the like.

The present invention will be further illustrated by the following preparations and examples. It should be understood, however, that the examples are given only for the purpose of illustration and not intended to limit the present invention in any way.

PREPARATION 1

Ethyl p-aminophenylacetate: Compound 1

In 15% hydrogen chloride-ethanol, p-aminophenylacetic acid was refluxed. After removal of ethanol by distillation, the residue was extracted with ethyl acetate and the extract was washed successively with water, saturated sodium bicarbonate solution and water and dried. The ethyl acetate was then distilled off to give p-aminophenylacetic acid ethyl ester.

PREPARATION 2

Ethyl 2-(4-aminophenyl)propionate: Compound 2

After washing 30.3 g of sodium hydride (50% mineral oil suspension) with n-hexane, it was suspended in 370 ml of N,N-dimethylformamide and was stirred under ice cooling. To this was added dropwise 100 g (0.574 mole) of diethylmethyl malonate and the mixture was stirred until the generation of hydrogen was stopped. Subsequently, a solution of 90.5 g (0.574 mole) of p-chloronitrobenzene in 145 ml of N,N-dimethylformamide was added dropwise and the mixture was heated at 80° C. on an oil bath for 10 hours. Thereafter, N,N-dimethylformamide was distilled off under reduced pressure and the residue was extracted with ethyl acetate. The ethyl acetate layer was washed with 5% hydrochloric acid and with a saturated solution of sodium chloride, and dried over anhydrous magnesium sulfate. The ethyl acetate was then distilled off under reduced pressure to give 148 g of crude diethyl-2-methyl-2-(4-nitrophenyl)malonate.

147 g of the crude diethyl 2-methyl-2-(4-nitrophenyl)-malonate was dissolved in 600 ml of ethanol, and to this was added a solution of 42.4 g (0.846 mole) of 93% sodium hydroxide in 400 ml of water and the solution was reacted at 50° C. for 3 hours. After that, to the reaction mixture was added 1 l of water and the formed oily substance and an aqueous layer were separated. The aqueous layer was acidified with conc. hydrochloric acid and was extracted with 700 ml of ethyl acetate. The ethyl acetate layer was washed with a saturated solution of sodium chloride and dried over anhydrous magnesium sulfate. After filtering out magnesium sulfate, ethyl acetate was distilled off to give 66.8 g of crude 2-(4-nitrophenyl)propionic acid.

23.3 g of the crude 2-(4-nitrophenyl)propionic acid was dissolved in 100 ml of 22% hydrochloric acid-ethanol solution, and the solution was refluxed on an oil bath for two hours. After ethanol was distilled off under reduced pressure, the residue was neutralized with a saturated solution of sodium bicarbonate and extracted with ethyl acetate. The ethyl acetate layer was washed with a saturated solution of sodium chloride and dried over anhydrous sodium sulfate. After distilling off ethyl acetate under reduced pressure, the residue was subjected to silica gel chromatography with chloroform solvent to give 55 g of ethyl 2-(4-nitrophenyl)propionate.

48.3 g (0.216 mole) of ethyl 2-(4-nitrophenyl)propionate was dissolved in 400 ml of ethanol and the solution was hydrogenated with 1 g of palladium black catalyst for 6 hours. Palladium black catalyst was filtered out and ethanol was distilled off to give 48.3 g of the remained oily substance. The oily substance was distilled under reduced pressure to give 38.6 g of ethyl 2-(4-aminophenyl)propionate as distillation fraction at 124°–126° C./1–2 mm Hg.

PREPARATION 3

Ethyl 2-(4-aminophenyl)-2-methylpropionate: Compound 3

After washing 10.56 g (equivalent to 0.22 mole) of sodium hydride (50% mineral oil suspension) with n-hexane, it was suspended in 100 ml of N,N-dimethylformamide and was stirred under ice cooling. A solution of 20.9 g (0.1 mole) of ethyl 4-nitrophenylacetate in 100 ml of N,N-dimethyl-formamide was added dropwise and the mixture was stirred under ice cooling for 1 hour and at room temperature for 2 hours. After distilling off N,N-dimethylformamide under reduced pressure, extracting with ethyl acetate and washing with 5% hydrochloric acid solution and further washing with a saturated solution of sodium chloride, the ethyl acetate layer was dried over anhydrous sodium sulfate. The ethyl acetate was distilled off under reduced pressure to give 20.33 g (0.086 mole) of ethyl 2-methyl-2-(4-nitrophenyl)propionate (Yield: 86%).

20.33 g of thus obtained ester was dissolved in 120 ml of ethanol and hydrogenated with 0.3 g of palladium black catalyst. After the palladium black was filtered out and ethanol was distilled off, the residue was dissolved in 5% hydrochloric acid solution and washed with ethyl acetate. The aqueous layer was neutralized with sodium carbonate and was extracted with ethyl acetate. The ethyl acetate layer was dried over anhydrous sodium sulfate. After distilling off ethyl acetate under reduced pressure, the residue was subjected to a silica gel chromatography with chloroform solvent to give 8.31 g (0.04 mole) of ethyl 2-(4-aminophenyl)-2-methylpropionate (Yield: 47%).

PREPARATION 4

Ethyl 4-acetylaminophenylacetate: Compound 4

To 179.2 g (1 mole) of ethyl p-aminophenylacetate was added 800 ml of ethyl acetate and it was made to a homogeneous solution with stirring at room temperature. To the solution was added a mixed solution of 103.4 ml (1.05 mole) of acetic anhydride (96%) and 100 ml of ethyl acetate and the solution was stirred for 3 hours. After completion of the reaction, the reaction mixture was washed with a saturated solution of sodium bicarbonate and also with a saturated solution of sodium chloride. After drying the ethyl acetate layer over anhydrous magnesium sulfate, ethyl acetate was distilled off. The residue was recrystallized from ethyl acetate-n-hexane to give 206.6 g of ethyl 4-acetyl-aminophenylacetate (Yield: 93.4%). M.P. 77°–78° C.

PREPARATION 5

Ethyl 2-(4-acetylaminophenyl)-2-methylpropionate: Compound 5

5.0 g of ethyl 2-(4-aminophenyl)-2-methylpropionate was dissolved in 50 ml of ethyl acetate, and 2.5 ml of acetic anhydride was added dropwise with stirring and the solution was still stirred in the same condition for 3 hours. The reaction mixture was washed with a saturated solution of sodium bicarbonate, and successively, with a saturated solution of sodium chloride, and the ethyl acetate layer was dried over anhydrous sodium sulfate. The ethyl acetate was distilled off under reduced pressure and the residue was recrystallized from ethyl acetate-n-hexane to give 4.61 g of ethyl 2-(4-acetylaminophenyl)-2-methylpropionate (Yield: 76%). M.P. 76.0°–76.5° C.

PREPARATION 6

Ethyl 4-(isobutyrylamino)phenylacetate: Compound 6

10 g of ethyl 4-aminophenylacetate was dissolved in 100 ml of benzene and to this was added 25 ml of water. To the solution were added dropwise a solution of 6 g of isobutyryl chloride in 20 ml of benzene and a solution of 2.4 g of 93% NaOH in 25 ml of water simultaneously under stirring over 15 minutes. After completion of the dropwise addition, the reaction mixture was stirred for 3 hours and allowed to stand at room temperature overnight. After separating the benzene layer, washing it with 1N-HCl solution and further washing with a saturated solution of sodium chloride, the benzene layer was dried over anhydrous sodium sulfate. After separating sodium sulfate by filtration, the solvent was distilled off under reduced pressure and the residue was dissolved in 30 ml of benzene and crystallized from 90 ml of n-hexane. The formed crystals were separated by filtration and were dried at a temperature below 60° C. under reduced pressure to give 12.3 g of ethyl 4-(isobutyrylamino)phenylacetate (Yield: 88.3%). M.P. 92.5°–93.5° C.

PREPARATION 7

Ethyl 4-(n-butyrylamino)phenylacetate: Compound 7

In accordance with Example 6 for reference, 10 g of ethyl 4-aminophenylacetate was reacted with 6 g of n-butyryl chloride similarly, and after treating it, 8.5 g of 4-(n-butyrylamino)phenylacetate was obtained. M.P. 72.5°–73.5° C.

PREPARATION 8

Ethyl 4-(4-methylbenzoylamino)phenylacetate: Compound 8

10 g of ethyl 4-aminophenylacetate was dissolved in 120 ml of benzene and to this was further added 25 ml of water. To this solution were added dropwise a solution of 8.6 g of p-toluoyl chloride dissolved in 20 ml of benzene and a solution of 2.4 g of 93% NaOH dissolved in 25 ml of water simultaneously under stirring over 15 minutes. After completion of the dropwise addition, the solution was stirred for 3 hours and allowed to stand overnight. After adding 200 ml of ethyl acetate, the oil layer was separated, washed with 1N-HCl solution and with a saturated solution of sodium chloride, and dried over anhydrous sodium sulfate. After distilling off the solvent, the residue was recrystallized from benzene-n-hexane to give 12 g of ethyl 4-(4-methylbenzoylamino)phenylacetate.

PREPARATION 9

Ethyl 2-(4-acetylaminophenyl)propionate: Compound 9

To 10 g (0.0517 mole) of ethyl 2-(4-aminophenyl)propionate was added 50 ml of ethyl acetate with stirring, and to this solution, a mixed solution of 5.81 g of acetic anhydride and 10 ml of ethyl acetate was added dropwise and was stirred for 3 hours. After completion of the reaction, the reaction mixture was washed with a saturated solution of sodium bicarbonate and with a saturated solution of sodium chloride. After the ethyl acetate layer was dried over anhydrous magnesium sulfate, the ethyl acetate was distilled off under reduced pressure. The residue was recrystallized from ethyl acetate-n-hexane to give 10.3 g of ethyl 2-(4-acetylaminophenyl)propionate (Yield: 85%). M.P. 94.5°–95.5° C.

PREPARATION 10

4-Acetylaminophenylacetate: Compound 10

To 110.6 g (0.5 mole) of ethyl 4-acetylaminophenylacetate was added 500 ml of water and the mixture was stirred at room temperature. To the solution was added 300 ml of 2N-NaOH and the mixture was stirred for 3 hours.

After completion of the reaction, the reaction system was cooled with ice and the crystals were formed by adding 100 ml of 20% hydrochloric acid solution. After stirring for 30 minutes under ice cooling, the formed crystals were collected by filtration, washed with cold water and dried to give 93.6 g of 4-acetylaminophenylacetic acid (Yield: 96.8%). M.P. 173°–175° C.

PREPARATION 11

2-(4-Acetylaminophenyl)-2-methylpropionic acid: Compound 11

3.87 g of ethyl 2-(4-acetylaminophenyl)-2-methylpropionate was dissolved in a mixed solution of 16.6 ml of 2N-caustic soda solution and 30 ml of ethyl alcohol and the solution was stirred at 50° C. for 8 hours. After distilling off ethyl alcohol under reduced pressure, the aqueous layer was extracted with ether and unreacted materials were removed. After the aqueous layer was acidified with conc. hydrochloric acid, the formed crystals were collected by filtration, washed with water, and recrystallized from acetone-water to give 2.15 g of 2-(4-acetylaminophenyl)-2-methylpropionic acid (Yield: 62%). M.P. 169.7°–170.8° C.

PREPARATION 12

In accordance with Example 10, the following carboxylic acids were obtained by hydrolyzing an ethyl carbonate corresponding to the carboxylic acid:
2-(4-Acetylaminophenyl)propionic acid: Compound 12
4-(Isobutyrylaminophenylacetic acid: Compound 13
4-n-Butyrylaminophenylacetic acid: Compound 14
4-(4-Methylbenzoylamino)phenylacetic acid: Compound 15

EXAMPLE 1

Effect on Plaque-forming Cells in Spleen against Sheep Erythrocytes in mice

Balb/c mice of 5 weeks old were intravenously immunized with $1 \times 10^8$ sheep erythrocytes/mouse. 5 mice were used per group. Medicament was orally administered for 4 days from the day when the mice were immunized. Mice were sacrificed on the 5th day and the numbers of plaque-forming cells (PFC) in the spleen against sheep erythrocytes were determined by Fujiwara's modified method of Cunningham's method ["Method in Immunological Experiment A" edited by Japanese Society for Immunology, page 1272 (1974)].

The results are as shown in Tables 2 and 3.

TABLE 2

| Medicaments | Dose (mg/kg) | PFC (× 2,500/spleen) Mean value ± Standard Error | % Control |
|---|---|---|---|
| Physiological saline solution | — | 64.2 ± 5.66 | — |
| Compound 10 | 30 | 116.4 ± 8.64** | 181 |
| Compound 10 | 100 | 107.2 ± 10.5** | 167 |
| Compound 10 | 300 | 82.2 ± 7.0 | 128 |

**P < 0.01

TABLE 3

| Medicaments | Dose (mg/kg) | PFC (× 3,125/spleen) Mean value ± Standard Error | % Control |
|---|---|---|---|
| Physiological saline solution | — | 66.4 ± 3.6 | — |
| Compound 1 | 30 | 89.4 ± 10.4 | 135 |
| Compound 1 | 100 | 60.6 ± 8.6 | 91 |
| Compound 1 | 300 | 82.0 ± 5.2* | 123 |

*P < 0.05

EXAMPLE 2

Effect on Sheep Erythrocytes induced Delayed Type Hypersensitivity

40 μl of Sheep erythrocytes adjusted to the concentration of $1 \times 10^7/40$ μl was subcutaneously injected to the right footpad of mice (ddY weighing 25–30 g) and the medicament was administered orally for continuous 4 days including the day, on which sheep erythrocytes were administered.

On the 4th day from the administration day of sheep erythrocytes, 40 μl of sheep erythrocytes adjusted to the concentration of $5 \times 10^8/40$ μl was subcutaneously injected to the left footpad. After 24 hours, both of the thickness of the right and left footpad were measured. Footpad swelling due to the delayed type hypersensitivity was recognized as the difference between the thickness of the left and right footpad. The footpad swelling of the medicament-administration group was compared with that of physiological saline solution-administration group (control group). The results are shown in Table 4.

TABLE 4

| Medicaments | Dose (mg/kg) | % Control of footpad swelling |
|---|---|---|
| Physiological saline solution | — | — |
| Azathioprine | 100 | 49.0** |
| Compound 10 | 30 | 77.0* |
|  | 100 | 85.7 |
|  | 300 | 71.6** |
| Compound 16 | 30 | 78.5** |
|  | 100 | 81.4 |
|  | 300 | 90.8 |
| Compound 1 | 30 | 79.8* |
|  | 100 | 85.9 |
|  | 300 | 77.9* |
| Compound 4 | 30 | 91.5 |
|  | 100 | 93.8 |

TABLE 4-continued

| Medicaments | Dose (mg/kg) | % Control of footpad swelling |
|---|---|---|
|  | 300 | 68.4* |

*P < 0.05
**P < 0.01

EXAMPLE 3

Effect on Methylated Human Albumin induced Delayed Type Hypersensitivity

100 μl of 0.25% methylated human albumin aqueous solution was injected subcutaneously to C3H mice of 5 weeks old. The medicament was administered orally for continuous 4 days including the immunization-day. On the 4th day from the immunization day, 25 μl of 0.1% methylated human albumin aqueous solution was subcutaneously injected to the footpad. After 24 hours, the thickness of the left and right footpad were measured, and the footpad swelling due to the delayed type hypersensitivity was represented as the difference between the thickness of the left and right footpad. The footpad swelling of the medicament-administration group was compared with that of physiological saline solution-administration group.

The results are shown in Table 5.

TABLE 5

| Medicaments | Dose (mg/kg) | Footpad swelling (× 0.01 mm) Mean value ± Standard error | % Control |
|---|---|---|---|
| EXPERIMENT 1 |  |  |  |
| Physiological saline solution | — | 63.3 ± 1.6 | — |
| Compound 10 | 300 | 44.5 ± 1.6** | 70.3 |
| Compound 6 | 30 | 59.0 ± 1.8 | 93.2 |
|  | 100 | 55.6 ± 1.2** | 87.8 |
|  | 300 | 56.8 ± 2.2* | 89.7 |
| Compound 13 | 30 | 57.2 ± 1.9* | 90.4 |
|  | 100 | 58.2 ± 1.9 | 91.9 |
|  | 300 | 58.5 ± 2.4 | 92.4 |
| Compound 15 | 30 | 54.2 ± 1.7** | 85.6 |
|  | 100 | 56.7 ± 1.8** | 89.6 |
|  | 300 | 57.4 ± 1.5* | 90.7 |
| EXPERIMENT 2 |  |  |  |
| Physiological saline solution | — | 58.4 ± 1.6 | — |
| Azathioprine | 100 | 41.4 ± 1.5** | 70.9 |
| Compound 10 | 30 | 46.1 ± 1.7** | 78.9 |
|  | 100 | 41.8 ± 2.5** | 71.6 |
|  | 300 | 42.3 ± 1.8** | 72.4 |
| Compound 12 | 30 | 54.5 ± 1.7 | 93.2 |
|  | 100 | 52.1 ± 1.5* | 89.2 |
|  | 300 | 52.4 ± 1.9* | 89.7 |
| Compound 9 | 30 | 51.4 ± 1.8** | 88.0 |
|  | 100 | 55.3 ± 2.0 | 94.7 |
|  | 300 | 56.0 ± 2.0 | 95.9 |
| Compound 11 | 30 | 54.5 ± 1.7 | 93.3 |
|  | 100 | 55.4 ± 1.8 | 94.9 |
|  | 300 | 51.3 ± 2.3* | 87.8 |
| Compound 14 | 30 | 50.9 ± 2.0** | 87.2 |
|  | 100 | 51.8 ± 1.4** | 88.7 |
|  | 300 | 56.7 ± 1.5 | 97.1 |
| EXPERIMENT 3 |  |  |  |
| Physiological saline solution | — | 64.0 ± 1.7 | — |
| Compound 16 | 30 | 57.2 ± 2.8* | 89.4 |
|  | 100 | 62.6 ± 3.1 | 97.8 |
|  | 300 | 50.7 ± 2.3** | 79.2 |
| Compound 4 | 30 | 48.3 ± 2.6** | 75.5 |
|  | 100 | 49.4 ± 3.5** | 77.2 |

TABLE 5-continued

| Medicaments | Dose (mg/kg) | Footpad swelling (× 0.01 mm) Mean value ± Standard error | % Control |
| --- | --- | --- | --- |
| | 300 | 56.5 ± 2.9* | 88.3 |

*P < 0.05
**P < 0.01

EXAMPLE 4

Effect on Rats Adjuvant Arthritis

Experiment method

10 Sprague Dawley male rats of 8 weeks old were used per one group, and 0.6 mg/0.05 ml of mycobacterium butyricum suspended in fluid paraffin was administered to the right posterior limb palm intradermally.

1 mg/kg–125 mg/kg of Compound 10 was administered orally from the previous day of the adjuvant injection for 27 days, and the volume of the palm was measured.

Results

From around the 10th day after adjuvant injection, so called, the secondary inflammation appeared. This appeared as swelling of limb, to which an adjuvant was injected and also as swelling of the limb, to which an adjuvant was not injected, and as nodes of auricle, tail and limbs.

Compound 10 showed the inhibitory activity especially at a low dose to these secondary inflammation.

Since the inhibitory activity of Compound 10 was very slight to the primary inflammation due to the direct action of the adjuvant, the changes of the relative swelling of the limb (%) to that on the 9th day are shown in FIG. 1.

The horizontal axis represents the numbers of days elapsed after the adjuvant was injected and the perpendicular axis represents the relative swelling (%) to that on the 9th day.

EXAMPLE 5

Acute Toxicity

The medicament was suspended in 3% "Tween-80" and the suspension was administered orally or intraperitoneally at a dose shown in Table 1 to mice (ddY weighing 20–25 g). The mortalities of mice treated with medicament on the 7th day after the administration are shown in Table 1.

TABLE 1

| Medicaments | Dose (mg/kg) | Administration routes | Numbers of died mice/ Numbers of mice used |
| --- | --- | --- | --- |
| Compound 6 | 5,000 | oral | 1/5 |
| | 1,000 | intra-peritoneal | 0/5 |
| Compound 13 | 5,000 | oral | 0/5 |
| | 1,000 | intra-peritoneal | 1/5 |
| Compound 15 | 5,000 | oral | 5/5 |
| | 1,000 | oral | 0/5 |
| | 1,000 | intra-peritoneal | 5/5 |
| | 300 | intra-peritoneal | 0/5 |
| Compound 12 | 5,000 | oral | 0/5 |
| | 1,000 | intra-peritoneal | 0/5 |
| Compound 9 | 1,500 | oral | 0/5 |
| | 1,000 | intra-peritoneal | 0/5 |
| Compound 11 | 5,000 | oral | 0/5 |
| | 1,000 | intra-peritoneal | 0/5 |
| Compound 14 | 1,000 | intra-peritoneal | 0/5 |
| Compound 10 | 5,000 | oral | 0/5 |
| | 1,000 | intra-peritoneal | 0/5 |
| Compound 1 | 3,000 | oral | 0/5 |
| | 1,000 | intra-peritoneal | 1/5 |

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A method of treating an autoimmune disease or an allergic disease, comprising:

administering to a subject suffering from said autoimmune disease a formulation of a pharmaceutically effective amount of a phenylacetic acid compound of the formula:

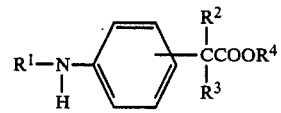

wherein $R^1$ is hydrogen or $C_{2-7}$ alkanoyl; $R^2$ and $R^3$ are each independently hydrogen of a $C_{1-4}$ alkyl; and $R^4$ is hydrogen or a $C_{1-4}$ alkyl group, or a pharmaceutically acceptable salt thereof, with pharmaceutically acceptable additives.

2. The method of claim 1, wherein from 1 to 3,000 mg per day of said phenylacetic acid compound is administered per day to said subject.

3. The method of claim 1, wherein said phenylacetic acid compound is administered orally, intramuscularly, subcutaneously, intravenously or rectally to said subject.

4. The method of claim 1, wherein said $C_{1-4}$ alkyl group of substituents $R^2$ to $R^4$ is selected from the group consisting of methyl, ethyl, n-propyl, isopropyl, n-butyl, isobutyl, and t-butyl.

5. The method of claim 1, wherein said $C_{2-7}$ alkanoyl substituent is methyl, ethyl, n-propyl, isopropyl, n-butyl, isobutyl, t-butyl or n-pentyl.

6. A method of treating a patient who requires immunomodulation, comprising:

administering to said patient an immunomodulating amount of a phenylacetic acid compound of the formula:

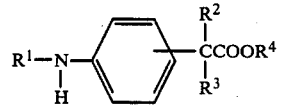

wherein $R^1$ is hydrogen or $C_{2-7}$ alkanoyl; $R^2$ and $R^3$ are each independently hydrogen or $C_{1-4}$ alkyl;

and $R^4$ is hydrogen or a $C_{1-4}$ alkyl group, or a pharmaceutically acceptable salt thereof.

7. The method of claim 6, wherein said phenylacetic acid compound or salt thereof is administered to said patient with pharmaceutically acceptable excipients.

8. The method of claim 6, wherein said phenylacetic acid compound is administered orally, intramuscularly, subcutaneously, intravenously or rectally to said subject.

9. The method of claim 6, wherein said $C_{1-4}$ alkyl group of substituents $R^2$ to $R^4$ is selected from the group consisting of methyl, ethyl, n-propyl, isopropyl, n-butyl, isobutyl, and t-butyl.

10. The method of clam 6, wherein said $C_{2-7}$ alkanoyl substituent is methyl, ethyl, n-propyl, isopropyl, n-butyl, isobutyl, t-butyl or n-pentyl.

11. An immunomodulating effective amount of a phenylacetic acid derivative of the formula (I):

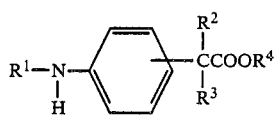

wherein $R^1$ is hydrogen or $C_{2-7}$ alkanoyl; $R^2$ and $R^3$ are each independently hydrogen or $C_{1-4}$ alkyl; and $R^4$ is hydrogen or a $C_{1-4}$ alkyl group, or a pharmaceutically acceptable salt of the acid in a pharmaceutically acceptable carrier.

12. The method of claim 1, wherein said autoimmune disease is chronic rheumatoid arthritis, systemic lupus erythematosus or collagen disease.

13. The method of claim 1, wherein said allergic disease is asthma.

* * * * *